United States Patent [19]

Siegemund et al.

[11] 4,454,072
[45] Jun. 12, 1984

[54] PROCESS FOR THE PREPARATION OF ω-FLUOROSULFATOPERFLUOROALKANOIC ACID DERIVATIVES

[75] Inventors: Günter Siegemund, Hofheim am Taunus; Werner Schwertfeger, Langgöns, both of Fed. Rep. of Germany

[73] Assignee: Hoechst Aktiengesellschaft, Frankfurt am Main, Fed. Rep. of Germany

[21] Appl. No.: 398,118

[22] Filed: Jul. 14, 1982

[30] Foreign Application Priority Data

Jul. 16, 1981 [DE] Fed. Rep. of Germany ....... 3128119

[51] Int. Cl.³ ............................................ C07C 141/00
[52] U.S. Cl. .................................................. 260/458 F
[58] Field of Search ..................................... 260/458 F

[56] References Cited

PUBLICATIONS

Earl et al., Inorg. Chem., 5, 2184 (1966).

"Preparation of an Acyl Fluoride, etc.", Lustig et al., Inorg. Chem. 3 (2), 287–288 (1964).
"Halogen Fluorosulfate Reactions, etc.", Shack et al., J. Fluorine Chemistry 16, 63–73 (1980).

*Primary Examiner*—Nicky Chan
*Attorney, Agent, or Firm*—Curtis, Morris & Safford

[57] ABSTRACT

What are disclosed are methods for making compounds of the formula

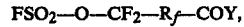

useful as intermediates for making perfluorinated vinyl ethers, wherein $R_f$ is a single bond or perfluoralkylene and Y is fluorine or —OR, by heating an α,ω-bis-fluorosulfatoperfluoroalkane of the formula

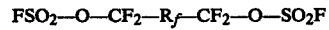

in the presence of an alkali metal fluoride and/or an alkali metal hydrogen fluoride and, when Y is OR, in the presence of an alkanol, ROH.

8 Claims, No Drawings

PROCESS FOR THE PREPARATION OF ω-FLUOROSULFATOPERFLUOROALKANOIC ACID DERIVATIVES

ω-Fluorosulfatoperfluoroalkanoic acid derivatives are compounds of the general formula:

$$FSO_2-O-R_f-CX$$

in which $R_f$ is an unbranched or branched perfluoroalkylene radical and

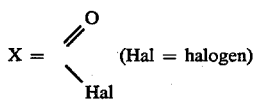  (Hal = halogen)

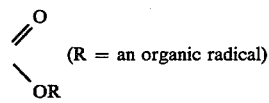  (R = an organic radical)

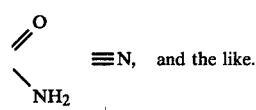  ≡N, and the like.

ω-Fluorosulfatoperfluorocarboxylic acid derivatives of the formula I $$FSO_2-O-(CF_2)_m-(CF_2-O-\underset{\underset{CF_3}{|}}{CF})_n-COA \quad (I)$$

in which A is halogen, preferably Cl or F, particularly F, or the group OR (R=an organic radical, in particular $CH_3$ or $C_2H_5$), m is 1-10 and n is 0-10, can be obtained in accordance with the process of Published German Patent Application No. 3,034,538 by (a) electrolyzing -H-perfluorocarboxylic acid halides of the formula II $$H(CF_2)_m-(CF_2-O-\underset{\underset{CF_3}{|}}{CF})_n-COA' \quad (II)$$

in which A' is halogen and m and n have the same meaning as in formula I, in an electrolyte composed of fluorosulfonic acid and an alkali metal fluorosulfonate, using platinum, or metals of the platinum group and/or vitreous carbon as anode materials and using cathode materials which are customary, but are stable under the conditions of electrolysis, isolating the ω-fluorosulfatoperfluorocarboxylic acid halides thus formed of the formula III $$FSO_2-O-(CF_2)_m-(CF_2-O-\underset{\underset{CF_3}{|}}{CF})_n-COA' \quad (III)$$

in which A' has the same meaning as in formula II and m and n have the same meaning as in the formulae I and II, and —in order to prepare the corresponding esters— b) esterifying these acid halides with an organic hydroxy compound of the formula IV $$ROH \quad (IV)$$

in which R has the meaning mentioned for formula I, to give ω-fluorosulfatoperfluorocarboxylic acid derivatives of the formula I in which A is OR.

The starting compounds for this process —ie. the ω-H-perfluorocarboxylic acid halides of the formula II—can be obtained, for example by the following known procedures:

1. J. Am. Chem. Soc. 74 (1952), 1426: The following triazine derivative

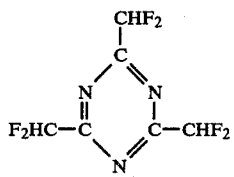

is prepared from ammonia and tetrafluoroethylene in the presence of copper acetate, and this derivative is then converted into the sodium salt of difluoroacetic acid $HCF_2$-COONa by heating with aqueous sodium hydroxide solution. The acid halides of the formula II (in which m is 1 and n is 0) can be obtained from this compound by known methods.

2. U.S. Pat. No. 2,559,629:

The preparation of aliphatic polyfluorocarboxylic acids and salts thereof by oxidizing perfluoroalkanols with permanganate:

$$H(CX_2CX_2)_nCH_2OH \xrightarrow{oxidation} H(CX_2CX_2)_nCOOH$$

X being Cl or F; at least half the radicals X being F, and n being 1-3.

The starting compounds for this oxidation reaction are prepared from ethylene derivatives $CX_2=CX_2$ and methanol.

The acid halides are obtained in a known manner from the resulting free acids; the compounds in which all the radicals X are F constitute the compounds of the formula II in which m is an even number and n is 0.

3. J. Org. Chem. volume 42, No. 25 (1977), 4055: describes, inter alia, the following reaction:

$$H(CF_2)_6CH_2OH \xrightarrow{oxidation}$$

$$H(CF_2)_6COOH \xrightarrow[\text{with } C_6H_5-COCl]{reflux}$$

$$H(CF_2)_6COCl \xrightarrow{+ \text{NaF in diglyme}}$$

$$H(CF_2)_6-COF \xrightarrow{+ CF_3-\overset{O}{\overset{/\backslash}{CF}}-CF_2}$$

$$H(CF_2)_6-CF_2-O-\underset{\underset{CF_3}{|}}{CF}-COF$$

The last three compounds in this series of reactions are all compounds of the formula II; the other compounds which fall under the formula II can also be obtained in a completely analogous manner.

The ω-fluorosulfatoperfluorocarboxylic acid esters which fall under the above formula I-ie. the compounds of the formula I':

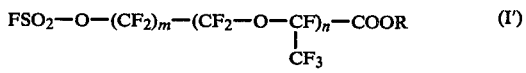

in which R is an organic radical, in particular $CH_3$ or $C_2H_5$, and m and n have the same meaning as in the formulae I–III, can then be converted, say by the process of Published German Patent Application No. 3,034,549 in the presence of catalytic quantities of an alkali metal fluoride and in the absence of solvents, into the corresponding perfluorinated dicarboxylic acid fluoride-esters of the formula V

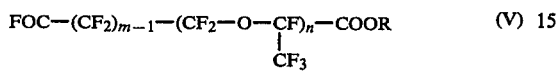

in which R, m and n have the abovementioned meaning.

The following reaction sequence, which is known per se: reaction with hexafluoropropene epoxide—saponification with an aqueous alkali metal hydroxide—and splitting off alkali metal fluoride and carbon dioxide by heating, makes it possible to obtain, from the perfluorinated dicarboxylic acid fluoride-esters of the formula V, perfluorinated vinyl ethers which still have an ester group at the other end of the molecule (=compounds of the formula VI):

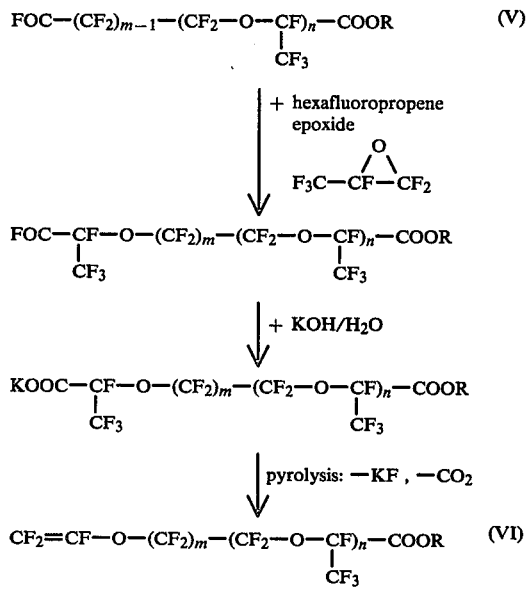

Perfluorinated vinyl ethers of this type which still have an ester group at the other end of the molecule are important monomers, the copolymers of which with tetrafluoroethylene and other fluoroolefins are used for the production of ion-selective membranes, cation exchange compositions and fluorocarbon elastomers.

In accordance with what has been said above, ω-fluorosulfatoperfluorocarboxylic acid derivatives (in particular the esters) and/or perfluorinated dicarboxylic acid fluoride-esters are thus important key substances for the preparation of perfluorinated vinyl ethers which still have a functional group at the other end of the molecule.

Perfluorinated aliphatic compounds of this type which have two different functional groups in the molecule, can, in principle, also be obtained, starting from perfluorinated aliphatic α,ω-bis-fluorosulfato compounds—by splitting off the two fluorosulfato groups, say by means of cesium fluoride CsF, and partial esterification of the dicarboxylic acid difluorides which result when these groups are split off; the following reactions are known:

1. J. Fluorine Chemistry 16, pages 63–73, in particular page 65 (1980):

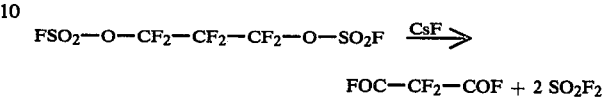

2. German Offenlegungsschrift No. 2,751,050: The preparation of perfluorinated dicarboxylic acid fluoride-esters by partially esterifying the corresponding perfluorinated dicarboxylic acid difluorides with an alcohol:

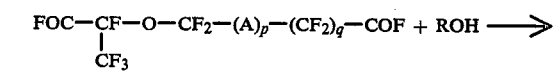

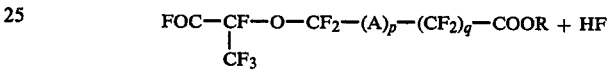

(A is a bifunctional $C_1$–$C_{10}$ perfluoro group, R is an organic radical, p is 0 or 1 and q is 1–8).

However, this partial esterification process does not take place selectively with to respect the perfluorinated dicarboxylic acid fluoride-esters, but always results in mixtures containing the isomeric half-esters, which are difficult to separate, and also the diesters, together with, in some cases, unreacted starting material.

Since the selective conversion of only one functional group in molecules containing 2 identical functional groups does not in most cases take place with the degree of completion desired-what is formed here in virtually every case is mixture of the desired compound in which one functional group has been modified and the compound in which both functional groups have been modified, and the starting compound, which can often only be separated by means of a considerable outlay—the method of partial esterification of perfluorinated discarboxylic acid difluorides did not appear to be as promising as could be wished for the preparation of perfluorinated dicarboxylic acid fluoride-esters.

The difficulties involved in the conversion of only one of two identical functional groups in a molecule, in fluorine chemistry in particular, also become evident from, for example, U.S. Pat. No. 4,181,679. As is emphasized several times in this U.S. patent, the authors of this publication were concerned with the preparation of ω-iodoperfluoroalkylene oxide acyl fluorides by the selective reaction of only one of 2 identical $CF_2I$ groups in the appropriate starting molecule to give the COF group by heating with zinc sulfate/sulfuric acid at temperatures of about 60° to 120° C., in accordance with the following schematic equation:

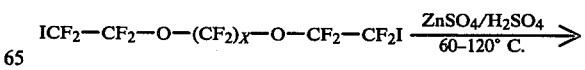

(x is an integer not less than 2).

As is apparent, in particular, from Example 3 of the patent, the desired product having 2 non-identical functional groups (namely the $CF_2I$ group and the COF group) in the molecule is obtained, at best, in a yield of only 35%.

Although the route to the perfluorinated vinyl ethers, desired as the final product, which still have one further functional group (in particular the ester group) in the molecule, via the ω-fluorosulfatoperfluorocarboxylic acid derivatives and the perfluorinated dicarboxylic acid fluoride-esters in accordance with the process of Published German Patent Application Nos. 3,034,548 and 3,034,549 is entirely feasible, and although the possible route indicated above, starting from α,ω-bis-fluorosulfatoperfluoroalkanes via the perfluorinated dicarboxylic acid difluorides and partial esterification of the latter also constitutes a practicable route, these methods are not completely satisfactory, partly because the starting materials (of the formula II for the process of the patent applications mentioned) are not entirely easy of access, and partly because the selective partial esterification of the corresponding perfluorinated dicarboxylic acid difluorides does not take place to the extent which is desirable and necessary.

The problem therefore presented itself of opening up an improved route to the perfluorinated vinyl ethers which still have one further functional group-in particular an ester group-in the molecule.

It has been possible to solve this problem, in accordance with the invention, by means of an improved method of preparing the ω-fluorosulfatoperfluoroalkanoic acid fluorides and esters which are used as intermediate products in this route. The invention therefore relates to a process for the preparation of ω-fluorosulfatoperfluoroalkanoic acid derivatives of the formula VII $$FSO_2-O-CF_2-R_f-COY \quad (VII)$$

in which $R_f$ is a single bond or an unbranched or branched perfluoroalkylene radical having 1-10, in particular 2-8, C atoms and Y is F or OR (R is an alkyl radical preferably containing 1-10 C atoms, in particular $CH_3$ or $C_2H_5$), starting from ω-fluorosulfato compounds, which comprises reacting α,ω-bis-fluorosulfatoperfluoroalkanes of the formula VIII $$FSO_2-O-CF_2-R_f-CF_2-O-SO_2F \quad (VIII)$$

in which $R_f$ has the same meaning as in formula VII, (a) in the presence of catalytic amounts of one or more alkali metal fluorides and/or alkali metal hydrogen fluorides at temperatures between about −30° and +150° C., with continuous removal of the initially formed compounds of the formula VII in which Y is F, or (b) in the presence of catalytic to approximately equimolar amounts of one or more alkali metal fluorides and/or alkali metal hydrogen fluorides and in the presence of an at least equimolar amount of an alcohol of the formula IX $$ROH \quad (IX)$$

in which R has the meaning mentioned for formula VII, and, if appropriate, also in the presence of an inert diluent which does not dissolve the alkali metal fluorides and/or alkali metal hydrogen fluorides, also within the temperature range between about −30° and +150° C., until an approximately equimolar amount of $SO_2F_2$ has been liberated, to give compounds of the formula VII in which Y is OR.

This procedure, which is simple per se, makes it possible, starting from the readily accessible α,ω-bis-fluorosulfatoperfluoroalkanes of the formula VIII, to split off selectively only one of the two fluorosulfato groups at yields of up to about 70% of theory (with the formation of the acid fluoride group or the ester group). In view of the inadequate selectivity of the known processes for reacting only one of two identical functional groups present in one and the same molecule, in particular in the field of organic fluorine compounds (cf. German Offenlegungsschrift No. 2,751,050 and U.S. Pat. No. 4,181,679), this result could not have been expected and was, therefore, extremely surprising.

The starting substances for the process according to the invention—the α,ω-bis-fluorosulfatoperfluoroalkanes of the formula VIII—can be obtained, for example, by the following methods:

1. J. M. Shreeve and G. H. Cady, J. Am. Chem. Soc. 83, pages 4521 to 4525, in particular page 4523 (1961): The gas-phase reaction of tetrafluoroethylene with peroxodisulfuryl difluoride $FSO_2-O-O-SO_2F$ to give 1,2-bis-fluorosulfatotetrafluoroethane:

$$CF_2=CF_2+FSO_2-O-O-SO_2F \rightarrow$$
$$FSO_2-O-CF_2CF_2-O-SO_2F$$

2. C. G. Krespan, J. Fluorine Chemistry 2, pages 173 to 179, in particular page 174 (1972/73): The gas-phase reaction of hexafluoropropene with peroxodisulfuryl difluoride to give a mixture of the corresponding 1:1 (62%) and 2:1 (22%) adducts:

$$CF_2=CF-CF_3 + FSO_2-O-O-SO_2F \longrightarrow$$

$$FSO_2-O-CF_2-\underset{\underset{CF_3}{|}}{CF}-O-SO_2F \ (62\%) +$$

$$FSO_2-O-(C_3F_6)_2-O-SO_2F \ (22\%)$$

3. C. J. Shack and K. O. Christe, J. Fluorine Chemistry 16, page 73 (1980): The reaction of α,ω-bis-bromoalkanes with chlorine fluorosulfate to give the corresponding α,ω-bis-fluorosulfatoperfluoroalkanes, for example:

$$Br-CF_2-CF_2-CF_2-Br+2ClOSO_2F \rightarrow$$
$$FSO_2-O-(CF_2)_3-O-SO_2F+2BrCl$$

4. A. Germain and A. Commeyras, Tetrahedron, volume 37, pages 487 to 491: The anodic oxidation of α,ω-bis-iodoperfluoroalkanes in an electrolyte composed of a solution of an alkali metal fluoride in fluorosulfonic acid. The authors are of the opinion that a direct electrode process takes place, but do not exclude a simultaneous, indirect process via "I+" (page 488, right-hand column).

5. In accodance with the process of Published German Patent Application No. 3,128,118, filed on July 16, 1981 α,ω-bis-fluorosulfatoperfluoroalkanes are obtained particularly advantageously from perfluorinated α-olefins and peroxodisulfuryl difluoride by passing the perfluorinated α-olefins into a liquid phase containing the peroxodisulfuryl difluoride, the concentration of the peroxodisulfuryl difluoride in the liquid phase being kept substantially constant within the concentration range from about 0.005 to 0.2, preferably from about 0.01 to 0.1 mole/l. In a preferred embodiment of this process, the perfluorinated α-olefins are passed into the liquid phase of an electrolytic cell in which peroxodisulfuryl difluoride is formed by electrolyzing a solution of an alkali metal fluorosulfonate in fluorosulfonic acid, and is supplemented continuously to the extent that it is consumed.

The process gives mainly the 2:1 adducts formed from the corresponding perfluorinated α-olefins and peroxodisulfuryl difluoride. Using tetrafluoroethylene as the starting olefin, the main product formed is, therefore, 1,4-bis-fluorosulfatoperfluorobutane:

2CF₂=CF₂+FSO₂—O—O—SO₂F→
FSO₂—O—(CF₂)₄—O—SO₂F

The catalysts in the process according to the invention are alkali metal fluorides and/or alkali metal hydrogen fluorides, the Na and K compounds being preferred.

In the case of variant (a) of the process according to the invention, a catalytic amount of the alkali metal fluoride and/or alkali metal hydrogen fluoride is sufficient-in general an amount between about 0.1 and 30 mole %, relative to the starting bis-fluorosulfatoperfluoroalkane VIII.

The use of a solvent is not, as a rule, advantageous in this case.

Possible reaction temperatures are, in principle, temperatures between −30° and +150° C., temperatures between about 20° and 120° C. being preferred.

The reaction can be carried out under normal pressure as well as under a reduced or elevated pressure.

In carrying out the reaction, the sequence in which the reactants are added to one another is unimportant for practical purposes. However, it is advantageous to ensure good mixing of the batch, by stirring, during the whole duration of the reaction.

It is preferable to add the starting bis-fluorosulfatoperfluoroalkane and the catalyst to one another and, if necessary, to heat the mixture until evolution of gas takes place. It is particulary important and essential here that the resulting ω-fluorosulfatoperfluoroalkanoic acid fluoride—ie. the compound of the formula VII in which Y is F— is removed continuously during the reaction; this is advantageously effected by distilling it off continuously through a column. The pressure for this distillation should advantageously be adjusted to a value such that the boiling point of the product distilled off is about 10° to 60° C. below the reaction temperature.

In process variant (b) a catalytic to approximately equimolar amount of alkali metal fluoride and/or alkali metal hydrogen fluoride can be used—in general an amount between about 0.1 and 100 mole %, preferably between about 1 and 30 mole %, relative to the starting bis-fluorosulfatoperfluoroalkane VIII.

The temperature and pressure conditions of this process variant are virtually the same as those of variant (a).

However, in case (b) it is advantageous also to add an inert diluent which does not dissolve the alkali metal fluorides and/or alkali metal hydrogen fluorides, in addition to an at least approximately equimolar quantity of the alcohol of the formula IX which is required as a reactant. Examples of diluents of this type which can be used are halogenated hydrocarbons, such as methylene chloride and the like.

An advantageous mode of carrying out variant (b) consists, for example, in combining the starting bis-fluorosulfatoperfluoroalkane VIII, the alcohol IX and the alkali metal fluoride and/or alkali metal hydrogen fluoride and also, if appropriate, the diluent at a low temperature and to warm the mixture slowly, or to allow it to warm up slowly. When approximately the calculated quantity of sulfuryl fluoride SO₂F₂ has been formed (measured, perhaps, by means of a gasometer), the alkali metal fluoride and/or alkali metal hydrogen fluoride is filtered off and the filtrate is washed with water until it is free of alcohol and acid, and is dried and distilled.

The ω-fluorosulfatoperfluorocarboxylic acid esters of the formula VII in which Y is OR are obtained in this variant.

If it is intended to process this ester further to give the corresponding perfluoroalkanedicarboxylic acid fluoride-ester, perhaps by splitting off the fluorosulfato group still remaining by means of an alkali metal fluoride, it is advantageous not to carry out a fractional distillation at the conclusion of working up the mixture from process variant (b), but only to fractionate the perfluoroalkanedicarboxylic acid fluoride-ester.

Since hydrofluoric acid is also formed as a reaction product, particularly in process variant (b), it is particularly advisable in this case to carry out the reaction in vessels made of a material resistant to hydrofluoric acid.

Because the starting bis-fluorosulfatoperfluoroalkanes of the formula VIII are accessible relatively simply and easily and because the process according to the invention can be carried out extremely easily and has a high selectivity and yield (up to about 70% of theory), this process constitutes a considerable advance in this field.

The invention will now be illustrated in greater detail by means of the examples which follow.

The examples A of the invention are followed by examples B of further processing, which relate to the further processing of the ω-fluorosulfatoperfluoroalkanoic acid derivatives prepared by the process according to the invention.

All the reactions are carried out in a fume cabinet:
¹H-NMR spectra: solvent CDCl₃; TMS [(CH₃)₄Si] as the internal standard
¹⁹F-NMR spectra: solvent CDCl₃; CFCl₃ as internal standard
(A) Examples of the invention
(Aa) Process variant a:
Preparation of ω-fluorosulfatoperfluoroalkanoic acid fluorides

Example 1

4-Fluorosulfatoperfluorobutyryl fluoride
FSO₂—O—(CF₂)₃—COF 2.9 g (0.05 mole) of dry potassium fluoride and 120 g (0.3 mole) of 1,4-bis-fluorosulfatoperfluorobutane were initially placed in a dry flask equipped with a magnetic stirrer, a thermometer, a Vigreux column, a fractionation head and a cold trap (−78° C.) located downstream. The mixture was heated at 80°–100° C. There was a vigorous evolution of gas and colorless liquid passed over, which was taken off without allowing reflux to take place. After the reaction, the cold trap contained 56 g of liquid. 38 g of this were volatile at +10° C. The residue was fractionated together with the distillate. This fractionation gave 10 g (17%) of perfluorobutanedioic acid difluoride and 45.5 g (51%) of 4-fluorosulfatoperfluorobutyryl fluoride (boiling point 83°–85° C./755 mm).

Analysis: Calculated: C 16.23; F 51.31; S 10.83. Found: C 16.3; F 51.3; S 11.5.

$^{19}$F-NMR: +51.1 (t, 1F, —O—SO$_2$F), +25.3 (m, 1F, —COF), −83.3 (q, 2F, —CF$_2$—O—), −118.6 (q, 2F, —CF$_2$—CO—), −125.7 (s, 2F, —CF$_2$—)

IR (gas spectrum): 5.28μ (C=O), 6.63μ (S=O).

Example 2

4-Fluorosulfatoperfluorobutyryl fluoride
FSO$_2$—O—(CF$_2$)$_3$—COF 398 g (1.0 mole) of 1,4-bis-fluorosulfatoperfluorobutane, 1.16 g (0.02 mole) of dry potassium fluoride and 0.84 g (0.02 mole) of sodium fluoride were placed in an apparatus as described in Example 1. The mixture was then heated at 100°–120° C. Gas evolution set in after a short time and reflux took place in the column. The liquid which passed over had a boiling point of 75°–80° C. Working up was carried out as in Example 1. 196 g (66%) of 4-fluorosulfatoperfluorobutyryl fluoride were obtained.

Example 3

6-Fluorosulfatoperfluorohexanoyl fluoride
FSO$_2$—O—(CF$_2$)$_5$—COF 200 g (0.4 mole) of 1,6-bis-fluorosulfatoperfluorohexane, 1.16 g (0.02 mole) of potassium fluoride and 1.68 g (0.04 mole) of sodium fluoride were placed in an apparatus as described under Example 1. The mixture was heated under a pressure of 200 mm Hg until gas evolution took place. The distillate which then passed over was taken off at such a rate that the boiling point did not exceed 90° C./200 mm. Working up was carried out as in Example 1. 11 g (9%) of perfluorohexanedioic acid difluoride, boiling point 73°–76° C./740 mm Hg, and 92.5 g (58%) of 6-fluorosulfatoperfluorohexanoyl fluoride, boiling point 126°–127° C./740 mm, were obtained.

Analysis: Calculated C 18.19; F 57.56; S 8.09. Found C 18.30; F 57.10; S 9.50.

$^{19}$F-NMR: +50.6 (t, 1F, —O—SO$_2$F), +24.8 (m, 1F, —COF), −83.3 (m, 2F, —O—CF$_2$—), −118.4 (m, 2F, —CF$_2$—CO—), −121.9 (m, 2F, CF$_2$), −122.8 (m, 2F, CF$_2$), −125.0 (m, 2F, CF$_2$).

IR (neat): 5.31μ (C=O), 6.68μ (S=O).

Example 4

8-Fluorosulfatoperfluorooctanoyl fluoride
FSO$_2$—O—(CF$_2$)$_7$—COF 100 g (0.17 mole) of 1,8-bis-fluorosulfatoperfluorooctane were heated with 0.58 g (0.01 mole) of potassium fluoride and 0.84 (0.02 mole) of sodium fluoride under a pressure of 50 mm in accordance with the working instructions of Example 3. Distillation through a packed column gave 42 g (51%) of 8-fluorosulfatoperfluorooctanoyl fluoride, boiling point 86°–87° C. (50 mm).

Analysis: Calculated: C 19.37; F 61.27; S 6.46. Found: C 19.60; F 60.20; S 7.50.

$^{19}$F-NMR: +50.6 (t, 1F, —O—SO$_2$F), +24.7 (m, 1F, —COF), −83.4 (m, 2F, —CF$_2$—O—), −118.7 (m, 2F, —CF$_2$—CO—), −122.2 (m, 6F, CF$_2$), −122.8 (m, 2F, CF$_2$), −125.0 (m, 2F, CF$_2$).

IR (neat): 5.31μ (C=O), 6.67μ (S=O).

(Ab) Process variant b:

The preparation of ω-fluorosulfatoperfluoroalkanoic acid esters which, however, in this case were immediately reacted further to give the corresponding perfluoroalkanedioic acid fluoride-ester by heating with alkali metal fluorides (leading to the fluorosulfato group being split off).

Example 5

Methyl 4-fluorosulfatoperfluorobutyrate
FSO$_2$—O—CF$_2$—CF$_2$—CF$_2$—COOCH$_3$ reacted further to give 3-carbomethoxyperfluoropropionyl fluoride FOC—CF$_2$—COOCH$_3$ 250 ml of methanol, 25.2 g (0.6 mole) of sodium fluoride and 240 g (0.6 mole) of 1,4-bis-fluorosulfatoperfluorobutane were placed, at −30° C., in a dry flask equipped with a magnetic stirrer, a thermometer, a reflux condenser and a bubble counter. The mixture was allowed to reach room temperature slowly, while stirring well. The bis-fluorosulfate reacted, liberating sulfuryl fluoride. Stirring was continued at room temperature until the lower phase had disappeared. After the precipitated salt had been filtered off, the filtrate was poured into ice-water. The organic phase was washed with water until free from acid and was dried over calcium chloride. Distillation through a short Vigreux column gave 159 g of colorless liquid, boiling point 142°–177° C./760 mm, which were reacted with 1.8 g (0.03 mole) of potassium fluoride in accordance with the instructions of Example 4. Distillation gave 81 g (65% relative to the bis-fluorosulfate employed) of 3-carbomethoxyperfluoropropionyl fluoride as well as small quantities of perfluorobutanedioic acid difluoride and dimethyl perfluorobutanedioate.

Example 6

Methyl 4-fluorosulfatoperfluorobutyrate
FSO$_2$—O—CF$_2$—CF$_2$—CF$_2$—COOCH$_3$, reacted further to give 3-carbomethoxyperfluoropropionyl fluoride FOC—CF$_2$—COOCH$_3$ 100 g (0.25 mole) of 1,4-bis-fluorosulfatoperfluorobutane were reacted, in accordance with the working instructions of Example 5, with 3.9 g (0.05 mole) of potassium hydrogen fluoride in a mixture of 100 ml of methanol and 100 ml of methylene chloride, initially at 0°–10° C. and later at approx. 20° C. When the gas evolution was complete, the salt was filtered off and the filtrate was worked up as described in Example A5. This gave 62 g of distillate, boiling point 139°–176° C./755 mm, which, after being reacted with 0.58 g (0.01 mole) of potassium fluoride, gave 24 g (46%) of 3-carbomethoxyperfluoropropionyl fluoride.

(B) Further processing examples

Example 1

Methyl 4-fluorosulfatoperfluorobutyrate
FSO$_2$—O—(CF$_2$)$_3$—COOCH$_3$

A solution of 35.2 g (1.1 moles) of methanol in 50 ml of methylene chloride was added dropwise, while stirring well, to a solution of 280 g (0.95 mole) of 4-fluorosulfatoperfluorobutyryl fluoride in 250 ml of methylene chloride, which was kept at 0°–10° C. The mixture was stirred for a further hour. It was then washed with water until free from acid, and the organic phase was dried over calcium chloride. When distilled through a packed column, 260 g (89%) of methyl 4- fluorosulfatoperfluorobutyrate were obtained, boiling point 71°–73° C./50 mm.

Analysis: Calculated: C 19.49; H 0.98; F 43.16; S 10.41. Found: C 19.8; H 1.0; F 42.7; S 10.6.

$^1$H-NMR: 3.98 (s, —O—CH$_3$).

$^{19}$F-NMR: +50.5 (t, 1F, —O—SO$_2$F), —83.5 (q, 2F, —O—CF$_2$), —119.0 (t, 2F, —CF$_2$—CO—), —126.2 (s, 2F, CF$_2$).

IR (neat): 3.41μ (CH), 5.55μ (C=O), 6.68μ (S=O).

Example 2

Methyl 6-fluorosulfatoperfluorohexanoate
FSO$_2$—O—(CF$_2$)$_5$—COOCH$_3$

A solution of 92 g (0.23 mole) of 5-fluorosulfatoperfluorohexanoyl fluoride in 75 ml of methylene chloride was reacted, as described in Example B1, with a solution of 9.6 g (0.3 mole) of methanol in 75 ml of methylene chloride. This gave 81 g (85%) of methyl 6-fluorosulfatoperfluorohexanoate, boiling point 75°–77° C./20 mm.

Analysis: Calculated C 20.60 H 0.74 F 51.20 S 7.86 Found C 20.3 H 0.5 F 50.9 S 8.3

$^1$H-NMR: 3.97 (s, —O—CH$_3$).

$^{19}$F-NMR: +50.5 (t, 1F, —O—SO$_2$F, J=8 Hz), —83.4 (m, 2F, —CF$_2$—O—), —118.8 (m, 2F, —CF$_2$—CO—), —122.2 (m, 2F, CF$_2$), —123.5 (m, 2F, CF$_2$), —124.9 (m, 2F, CF$_2$).

IR (neat): 3.42μ (CH), 5.68μ (C=O), 6.69μ (S=O).

Example 3

Methyl 8-fluorosulfatoperfluorooctanoate
FSO$_2$—O—(CF$_2$)$_7$—COOCH$_3$

A solution of 5.5 g (0.17 mole) of methanol in 100 ml of methylene chloride was reacted, in accordance with the working instructions of Example B1, at 0° to 10° C. with 78 g (0.16 mole) of 8-fluorosulfatoperfluorooctanoyl fluoride. Distillation gave 72 g (90%) of methyl 8-fluorosulfatoperfluorooctanoate, boiling point 86°–87° C./10 mm.

Analysis: Calculated: C 21.27; H 0.60; F 56.08; S 6.31. Found: C 21.2; H 0.6; F 55.9; S 5.9.

$^1$H-NMR: 3.96 (s, —O—CH$_3$).

$^{19}$F-NMR: +50.7 (t, 1F, —OSO$_2$F, J=8 Hz), —83.3 (m, 2F, —O—CF$_2$—), —118.8 (m, 2F, —CF$_2$—CO—), —122.2 (m, 6F, —CF$_2$—), —123.0 (m, 2F, —CF$_2$—), —126.0 (m, 2F, —CF$_2$—)

IR (neat): 3.41μ (CH), 5.56μ (C=O), 6.68μ (S=O).

Example 4

3-Carbomethoxyperfluoropropionyl fluoride
CH$_3$OOC—(CF$_2$)$_2$—COF 260 g (0.84 mole) of 4-fluorosulfatoperfluorobutyryl fluoride and 2.9 g (0.05 mole) of dry potassium fluoride were initially taken in a dry flask equipped with a magnetic stirrer, a thermometer, a reflux condenser and a bubble counter. The mixture was heated until gas evolution began. The sulfuryl fluoride was split off between 70° and 100° C. When the evolution of gas was complete, the liquid remaining in the flask was distilled through a packed column. 169 g (97%) of 3-carbomethoxyperfluoropropionyl fluoride were obtained, boiling point 98°–99° C./755 mm.

Example 5

5-Carbomethoxyperfluoropentanoyl fluoride
CH$_3$OOC—(CF$_2$)$_4$—COF 130 g (0.32 mole) of methyl 6-fluorosulfatoperfluorohexanoate were reacted, in accordance with the instructions of Example B4, with 0.58 g (0.01 mole) of dry potassium fluoride. The sulfuryl fluoride was split off between 80° and 120° C. Distillation gave 94 g (96%) of 5-carbomethoxyperfluoropentanoyl fluoride, boiling point 62°–63° C./48 mm.

Example 6

7-Carbomethoxyperfluoroheptanoyl fluoride
CH$_3$OOC—(CF$_2$)$_6$—COF 67 g (0.13 mole) of methyl 8-fluorosulfatoperfluorooctanoate were heated with 0.58 g (0.01 mole) of potassium fluoride in accordance with the working instructions of Example B4. The sulfuryl fluoride began to be split off at approx. 80° C. Subsequent distillation gave 47 g (88%) of 7-carbomethoxyperfluoroheptanoyl fluoride, boiling point 88°–90° C./50 mm.

$^1$H-NMR: 3.94 (s).

$^{19}$F-NMR: +24.9 (m, 1F, COF), —118.8 (m, 4F, —CF$_2$—CO—), —122.1 (m, 4F, CF$_2$), —123.1 (m, 4F, CF$_2$)

IR (neat): 5.31μ (COF), 5.57μ (—COO—).

What is claimed is:

1. A method for making an ω-fluorosulfatoperfluoroalkanoic acid fluoride of the formula FSO$_2$—O—CF$_2$—R$_f$—COF, wherein R$_f$ is a single bond or branched or unbranched perfluoroalkylene, which method comprises heating an α,ω-bis-fluorosulfatoperfluoroalkane of the formula FSO$_2$—O—CF$_2$—R$_f$—CF$_2$—O—SO$_2$F at a temperature from —30° C. to 150° C. in the presence of a catalytic amount of at least one member selected from the group consisting of alkali metal fluorides and alkali metal hydrogen fluorides while continuously removing the ω-fluorosulfatoperfluoroalkanoic acid fluoride formed.

2. A method as in claim 1 wherein R$_f$ is perfluoroalkylene having 1 to 10 carbon atoms.

3. A method as in claim 1 wherein R$_f$ is perfluoroalkylene having 2 to 8 carbon atoms.

4. A method as in claim 1 wherein said ω-fluorosulfatoperfluoroalkanoic acid fluoride formed is removed by distillation at a temperature which is about 10 to 60 Centigrade degrees lower than the reaction temperature.

5. A method for making an ω-fluorosulfatoperfluoroalkanoic acid ester of the formula FSO$_2$—O—CF$_2$—R$_f$—COR, wherein R$_f$ is a single bond or branched or unbranched perfluoroalkylene and R is alkyl, which method comprises heating an α, ω-bis-fluorosulfatoperfluoroalkane of the formula FSO$_2$—O—CF$_2$—R$_f$—CF$_2$—O—SO$_2$F at a temperature from —30° C. to 150° C. in the presence of an at least equimolar amount of an alcohol, ROH, and in the further presence of a catalytic amount to an approximately equimolar amount of at least one member selected from the group consisting of alkali metal fluorides and alkali metal hydrogen fluorides until an approximately equimolar amount of sulfuryl fluoride, $SO_2F_2$, has been liberated.

6. A method as in claim 5 wherein $R_f$ is perfluoroalkylene having 1 to 10 carbon atoms.

7. A method as in claim 5 wherein $R_f$ is perfluoroalkylene having 2 to 8 carbon atoms.

8. A method as in claim 5 wherein an inert diluent which does not dissolve said alkali metal fluoride or alkali metal hydrogen fluoride is additionally present.

* * * * *